United States Patent [19]

Crittenden et al.

[11] Patent Number: 5,163,903
[45] Date of Patent: Nov. 17, 1992

[54] CATHETER EXCHANGE SYSTEM WITH DETACHABLE LUER FITTING

[75] Inventors: James F. Crittenden, Hollis, N.H.; George J. Purtell, Dracut, Mass.

[73] Assignee: C. R. Bard, Inc., Murray Hill, N.J.

[21] Appl. No.: 737,321

[22] Filed: Jul. 29, 1991

Related U.S. Application Data

[63] Continuation of Ser. No. 303,549, Jan. 27, 1989, Pat. No. 5,035,686.

[51] Int. Cl.$^5$ .............................................. A61M 29/00
[52] U.S. Cl. ........................................................ 604/96
[58] Field of Search ................... 604/96, 97, 98, 100, 604/243, 283; 128/344; 285/322, 334.4, 423; 606/194

[56] References Cited

U.S. PATENT DOCUMENTS

| | | | |
|---|---|---|---|
| 3,752,510 | 8/1973 | Windischman et al. | 285/334.4 |
| 4,187,848 | 2/1980 | Taylor | 604/243 |
| 4,270,778 | 6/1981 | Brownell | 285/305 |
| 4,290,428 | 9/1981 | Durand et al. | 604/96 |
| 4,299,226 | 11/1981 | Banka | 128/344 |
| 4,323,065 | 4/1982 | Kling | 128/214 R |
| 4,467,790 | 8/1984 | Schiff | 128/1 D |
| 4,547,194 | 10/1985 | Moorehead | 604/283 |
| 4,732,163 | 3/1988 | Bonello et al. | 128/772 |
| 4,736,733 | 4/1988 | Adair | 128/6 |
| 4,748,982 | 6/1988 | Horzewski et al. | 128/344 |
| 4,848,344 | 7/1989 | Sos et al. | 128/344 |
| 4,955,895 | 9/1990 | Sugiyama et al. | 606/194 |

FOREIGN PATENT DOCUMENTS

| | | |
|---|---|---|
| 0213748 | 3/1987 | European Pat. Off. |
| 8504432 | 10/1985 | PCT Int'l Appl. |
| 8606285 | 11/1986 | PCT Int'l Appl. |
| 8800844 | 2/1988 | PCT Int'l Appl. |
| 8801885 | 3/1988 | PCT Int'l Appl. |
| 627828 | 10/1978 | U.S.S.R. |
| 2180454 | 8/1989 | United Kingdom |

OTHER PUBLICATIONS

"Abdominal Aortography: A New Catheter Tip Closing Obturator for Percutaneous Technique", Straube et al., Radiology, vol. 81, No. 2, pp. 264-266, Aug. 1963.
Page from USCI 1969 Products Catalog—"Straube Tip Occluder Assembly".

Primary Examiner—John D. Yasko
Attorney, Agent, or Firm—Wolf, Greenfield & Sacks

[57] ABSTRACT

A small diameter balloon dilatation catheter having a shaft formed from hypodermic tubing is provided with a detachable luer fitting on its proximal end. The luer fitting may be removed and an extension wire attached to the proximal end of the catheter. A larger diameter catheter then may be advanced over the smaller catheter utilizing the smaller catheter to guide the larger catheter to the stenosis being treated. In another aspect of the invention, a guiding sheath assembly is provided which permits catheter exchanges involving such small diameter catheters having integral guidewires. In one protocol such a catheter may be exchanged for a conventional balloon dilatation catheter with a movable guidewire by removing the dilatation catheter, advancing the sheath over the guidewire, then removing the guidewire and inserting the replacement catheter. Similarly, a catheter having an integral guidewire may be exchanged for a similar catheter by first removing the luer fitting at the proximal end of the catheter, then attaching a wire extension to the proximal end of the catheter, then advancing a sheath over the extension and catheter to locate the distal end of the sheath in proximity to the stenosis, then removing the catheter through the sheath and replacing that catheter with a new catheter inserted through the sheath.

7 Claims, 6 Drawing Sheets

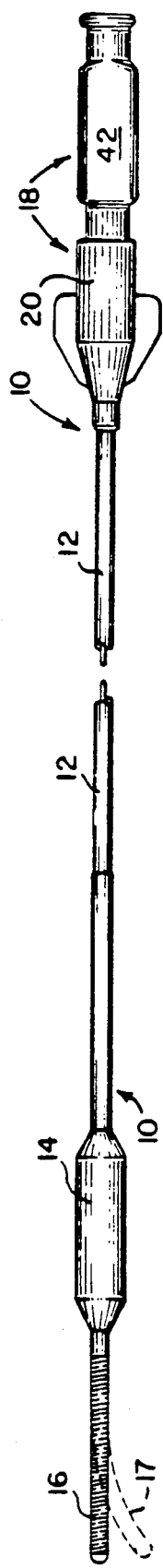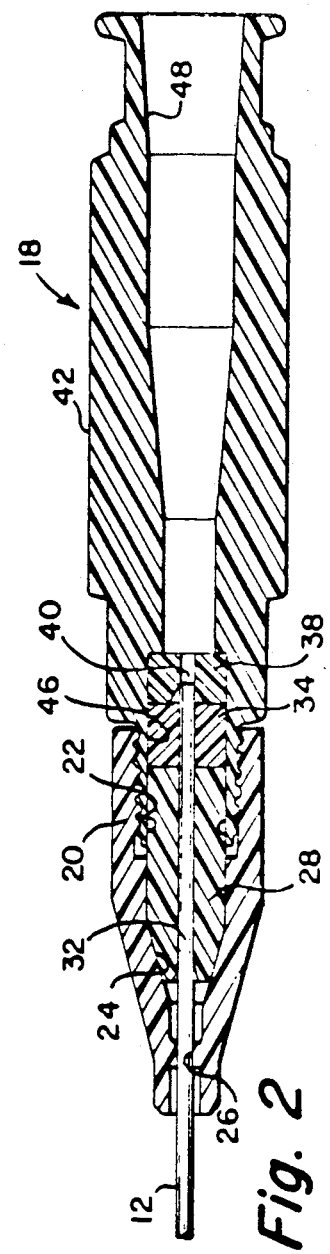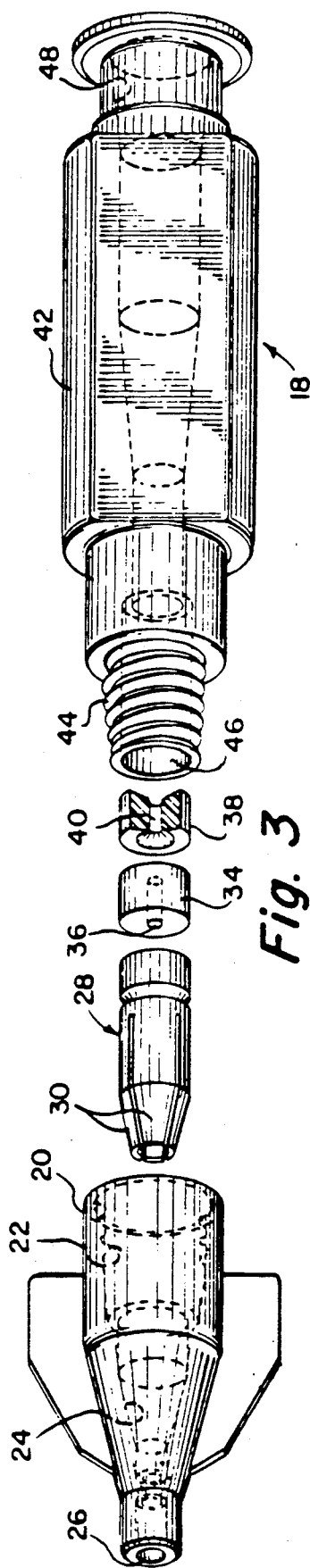

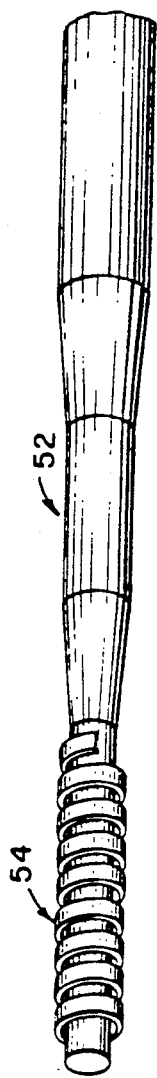
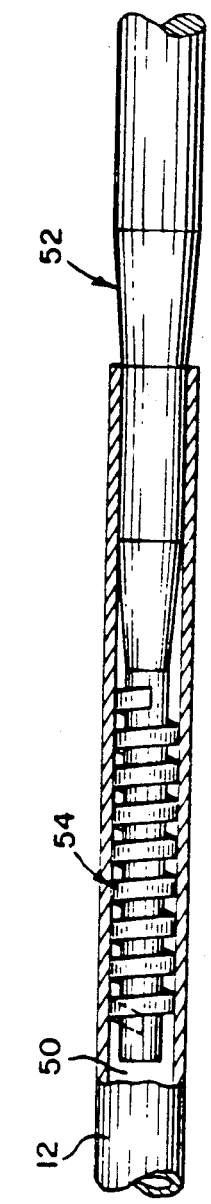
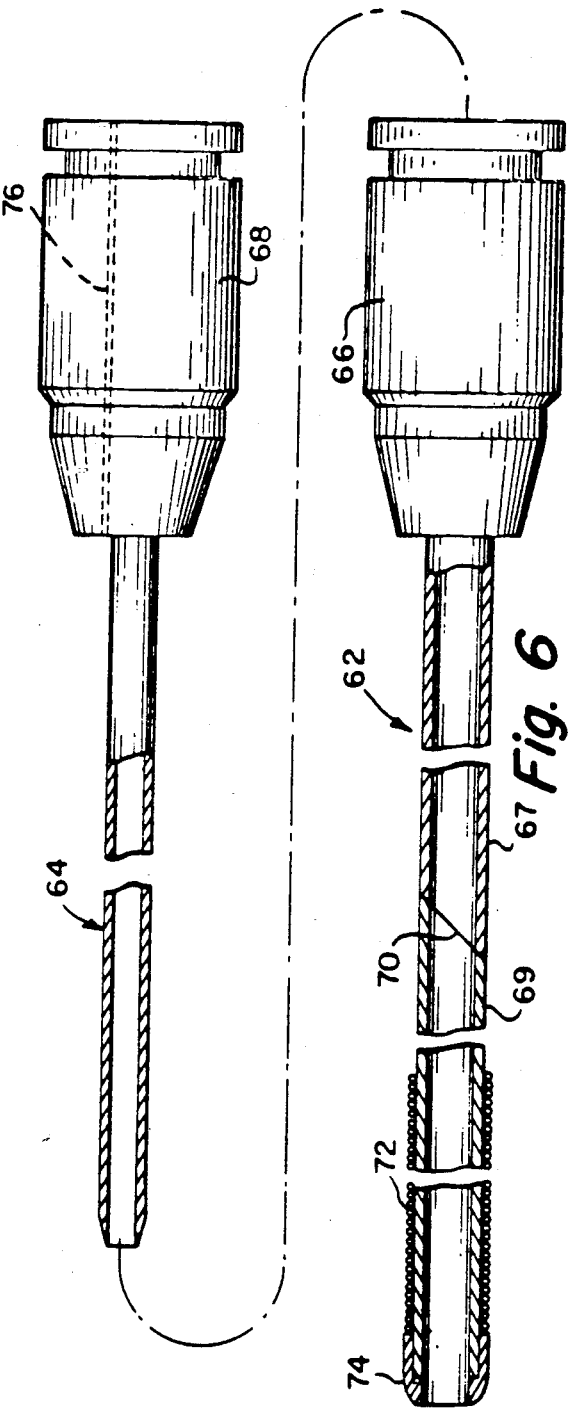

CATHETER EXCHANGE SYSTEM WITH DETACHABLE LUER FITTING

This application is a continuation of application Ser. No. 07/303,549, filed Jan. 27, 1989, now U.S. Pat. No. 5,035,686.

FIELD OF THE INVENTION

This invention relates to balloon dilatation catheter systems used in percutaneous transluminal coronary angioplasty.

BACKGROUND OF THE INVENTION

This invention relates to improvements in small diameter low profile dilatation catheters used in angioplasty and particularly coronary angioplasty. More particularly, the invention concerns the type of dilatation catheter which incorporates a wire-like shaft that is sufficiently torsionally rigid so as to be steerable thereby enabling the catheter to be selectively guided and steered to the desired location in the patient's coronary arteries.

In performing coronary angioplasty, it often occurs that the physician may wish to use a catheter different than the on originally inserted into the patient. For example, this may occur if the initial selection of catheter balloon size was inappropriate to treat the patient's stenosis or some other event occurs that would make use of a different catheter desirable. When the catheter is of the type that uses a separate movable guidewire, the catheter may be exchanged in a well known procedure in which an exchange wire is substituted for the movable guidewire (or the length of the guidewire is extended with an extension wire); then the catheter is withdrawn over the exchange wire and the replacement catheter is threaded over the exchange wire and is thereby guided to the stenosis. By maintaining the guidewire in position during the exchange procedure, the replacement catheter is easily and quickly advanced to the stenosis.

The foregoing catheter exchange procedure has not been usable with small diameter low profile dilatation catheters of the type that incorporate an integral guidewire because the balloon catheter cannot be separated from the guidewire. Thus, when it is desired to exchange one such dilatation catheter for another, the typical procedure is to withdraw the entire catheter and integral guidewire and then replace it with the desired catheter. Withdrawal of the catheter, however, results in loss of position of the catheter in the stenosis. As a result, the next placed catheter must be re-manipulated through the patient's arterial system to position the balloon in the stenosis. The replacement of the catheter typically involves time consuming manipulation and steering to guide the catheter to place its balloon within the stenosis. The additional procedure increases somewhat the risk of trauma to the patient.

A similar problem is presented when it is desired to exchange a conventional movable guidewire dilatation catheter for a catheter of the type having an integral guidewire. Again, in order to make such an exchange, it has been necessary to remove completely the movable guidewire and the dilatation catheter to permit insertion of the integral guidewire type of catheter. Because there is nothing to guide the catheter directly to the stenosis, it is necessary for the physician to go through all the manipulations necessary to steer and guide the new catheter to the stenosis.

It would be desirable, therefore, to provide a system by which catheter exchanges involving small diameter low profile dilatation catheters having an integral guidewire could be effected easily, quickly, without loss of position and with minimal trauma. It is among the objects of the invention to provide such a system.

SUMMARY OF THE INVENTION

In accordance with one aspect of the invention, a small diameter coronary dilatation catheter has a shaft formed from stainless steel hypodermic tubing. The distal end of the shaft is of increasing flexibility and terminates in a highly flexible distal tip. The dilatation balloon is mounted to the shaft near the distal end. The interior of the balloon is in communication with the lumen extending through the hollow shaft. The balloon may be inflated and deflated with a liquid by a syringe or other suitable inflation device attached to the proximal end of the shaft by a luer fitting carried at the proximal end of the shaft. In the present invention, the luer fitting is detachable from the hypodermic tubing so as to present a smooth continuous diameter at the proximal end of the catheter shaft. The luer fitting includes a collet and nut arrangement by which the luer fitting can grip securely the tubular proximal end of the dilatation shaft. After the luer fitting is detached, an extension wire is connected to the proximal end of the catheter shaft to extend its length. With its length so extended, a new catheter is advanced over the extension and along the shaft, following the shaft which thus serves as a guidewire to guide the catheter to the arterial branch to be treated. The small diameter dilatation catheter may remain in the patient and may serve as a guidewire for the larger catheter should it be desired to direct the larger catheter to other regions in the coronary anatomy. Should it be desired to again use the small diameter dilatation catheter with integral guidewire, the outer catheter and extension wire can be removed and the luer fitting can be replaced on the proximal end of the small diameter dilatation catheter to enable it to be used again to dilate a narrow stenosis.

Should it be desired to replace the small diameter dilatation catheter with another catheter also having an integral guidewire, the luer fitting is detached from the proximal end of the shaft and an extension wire is attached to the proximal end of the catheter shaft. In another aspect of the invention, an elongate flexible sheath then is advanced over the extended length dilatation catheter and into the patient's coronary artery close to the site of the stenosis. The dilatation catheter then is withdrawn through the sheath which remains in place. The new catheter then can be advanced through the sheath directly to the location in the coronary artery to be treated. In this instance, the sheath serves to maintain direct and quick access to the branch artery being treated.

In still another protocol that may be practised in accordance with the invention, a conventional dilatation catheter having a removable guidewire may be exchanged for the small diameter fixed guidewire type of dilatation catheter described above. In this aspect of the invention, an extension is fitted to the guidewire. Then the conventional dilatation catheter is removed from the patient, leaving the guidewire in place within the stenosis. The elongate flexible sheath, discussed above, then is advanced over the guidewire to the location of the stenosis. The guidewire and extension then may be removed and the catheter with integral guidewire may be inserted into the sheath and be guided directly to the stenosis.

It is among the general objects of the invention to provide an improved system for performing catheter exchanges involving a small diameter dilatation catheter having an integral guidewire.

Another object of the invention is to provide a small diameter dilatation catheter having a guidewire like tubular shaft in which a luer fitting at the proximal end of the shaft is detachable.

DESCRIPTION OF THE DRAWINGS

The foregoing and other objects and advantages of the invention will be appreciated more fully from the following further description thereof with reference to the accompanying drawings wherein:

FIG. 1 is a fragmented illustration of a small diameter dilatation catheter having an integral guidewire-like shaft;

FIG. 2 is an enlarged cross sectional illustration of the proximal end of the dilatation catheter shaft and the luer fitting;

FIG. 3 is an exploded illustration of the luer fitting;

FIG. 4A is an illustration of the ends of the extension wire and the proximal end of the dilatation catheter after the luer fitting is removed from the dilatation catheter and before the catheter and wire are joined;

FIG. 4B is a cross-sectional illustration of the connection between the guidewire extension and proximal end of the catheter;

FIG. 6 is a diagrammatic illustration of the system of a flexible guiding sheath and inner sheath which may be used to facilitate exchanges of dilatation catheters having an integral guidewire;

DESCRIPTION OF THE ILLUSTRATIVE EMBODIMENTS

Figure 5:
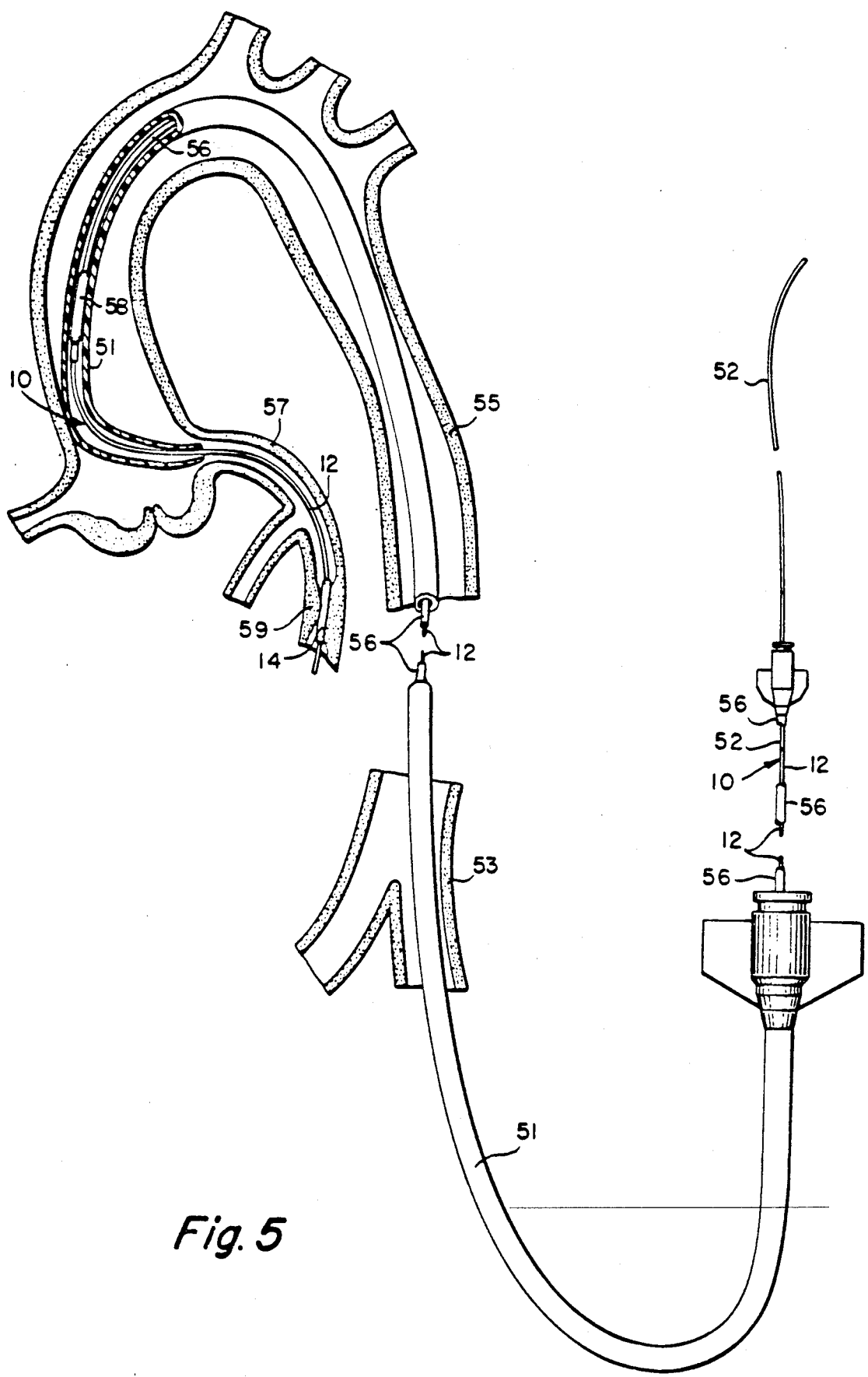
FIG. 5 is a diagrammatic illustration of a larger catheter being passed over the shaft of the smaller diameter dilatation catheter, with the shaft serving as a guidewire to guide the larger catheter to the stenosis.

FIG. 1 illustrates, generally, a small diameter balloon dilatation catheter 10. The catheter may be of the order of 175 cm long. It includes an elongate shaft 12 formed from hypodermic tubing. A polymeric dilatation balloon 14 is mounted to the distal end of the catheter. The distal tip 16 of the catheter is of increasing flexibility in a distal direction and, typically, may be formed from a helical coil of radiopaque material. The shaft 12 is sufficiently torsionally rigid so that it may transmit rotation from the proximal to the distal end of the catheter when the distal end is in the coronary arteries. In order that the device may be selectively steered through the branches of the coronary anatomy, the distal tip 16 is formed so that it may be bent to a slight "J" shape illustrated in phantom at 17. A luer fitting 18 is attached to the proximal end of the shaft 12 to enable attachment of an inflation device such as a syringe (not shown) to inflate and deflate the balloon 14 with a suitable fluid, such as radiopaque contrast liquid. Such a catheter is disclosed in more detail in U.S. patent application Ser. No. 729,541, filed May 2, 1985.

As shown in FIGS. 2 and 3, the luer fitting, indicated generally at 18, includes a hub 20 having a socket 22 at its proximal end and a distally tapering bore 24 located distally of the socket 22. An aperture 26 is formed at the distal end of the hub 20 and receives the proximal end of the catheter shaft 12. A collet 28 having distally extending fingers 30 is provided with a central bore 32, also to receive the proximal end of the shaft 12 of the catheter. A compressible gasket 34 formed from an elastomeric material such as silicone rubber, and also provided with a central bore 36, abuts the proximal face of the collet 28. The bore 36 of the gasket 34 receives the proximal end of the catheter shaft 12. A shaft stop member 38 is provided with a central aperture 40 which tapers in a proximal direction. The bore 40 tapers to a diameter that is smaller than the diameter of the proximal end of the catheter shaft 12 and, therefore, serves as an abutment for the proximal end of the shaft 12 as shown in FIG. 2, to prevent it from extending proximally beyond the stop member 38. The collet 28, gasket 34 and stop member 38 are securely retained between the hub 20 and a luer body 42 having a threaded distal end 44 that screws into the socket 22 of the hub 20. The distal end of the luer body 42 has a socket 46 which receives stop member 38, the gasket 34 and the proximal portion of the collet 28. The distal fingers 30 of the collet bear against the tapered bore 24 in the nut. When the luer body 42 is screwed into the nut 20, the collet fingers 30 constrict about the proximal end of the shaft 12 to securely lock the luer fitting 18 in place. The gasket 34 also is compressed to effect a secure liquid seal about the shaft 12. The proximal end of the luer body 42 has a luer socket 48 adapted to be connected to a syringe or other inflation/deflation device. Thus, it will be appreciated that the entire luer fitting 18 may be detached from the proximal end of the shaft 12 simply by unscrewing the hub 20 and luer body 42 to release the collet and permit the assembly to slide off of the proximal end of the shaft 12.

In accordance with the invention, the proximal end of the shaft 12 is formed to define a socket 50 adapted to receive the distal end of an extension wire 52 as illustrated in FIGS. 4A and 4B. The distal end of the extension wire is constructed in a manner that enables it to be detachably connected to the socket 50 in a manner described in detail in pending application Ser. No. 206,008 filed Jun. 13, 1988 entitled Removable Guidewire Extension, reference being made to said application for the full details of the extension wire connection. FIGS. 4A and 4B illustrate, somewhat diagrammatically, the nature of the connection. In brief, the distal end of the extension wire carries a helical coil 54 that detachably connects within the socket 50.

One manner in which the system may be used is illustrated in FIG. 5. In accordance with accepted percutaneous transluminal coronary angioplasty techniques, a guide catheter 51 is percutaneously inserted into a femoral artery 53 in the region of the groin and is advanced along the aorta 55 to place the distal tip of the guide catheter 51 at the entrance to the coronary artery 57. Once the guide catheter is in place, a balloon dilatation catheter 10 is advanced through the guide catheter 51 and is manipulated to position its balloon 14 within the the stenosis 59 to be treated. Should the physician wish to change to a larger catheter having a larger balloon, the inflation device is detached from the luer fitting and the luer fitting 18 is detached from the catheter shaft 12 by unscrewing the luer body 42 to loosen the fitting 18. The extension wire 52 then is attached to the socket 50 at the proximal end of the catheter shaft 12. The larger catheter 56 then may be advanced over the extension wire 52 and the catheter shaft 12 which guides the larger catheter 56 through the coronary arteries 57 directly to the stenosis 59. Depending on the dimensions of the catheters and the extent to which the balloon 14 on the small diameter dilatation catheter 10 can be collapsed, the larger catheter 56 may be passed over the balloon portion 14 of the smaller catheter 10. Alternately, the balloon 58 of the larger catheter 56 can be placed in the stenosis by advancing both the smaller and larger catheters 10, 56 distally until the balloon 58 of the larger catheter 56 is in the stenosis (if the coronary anatomy permits). The balloon 58 of the larger catheter 56 then may be inflated to perform the further dilatation with the larger size balloon.

Figure 7A:
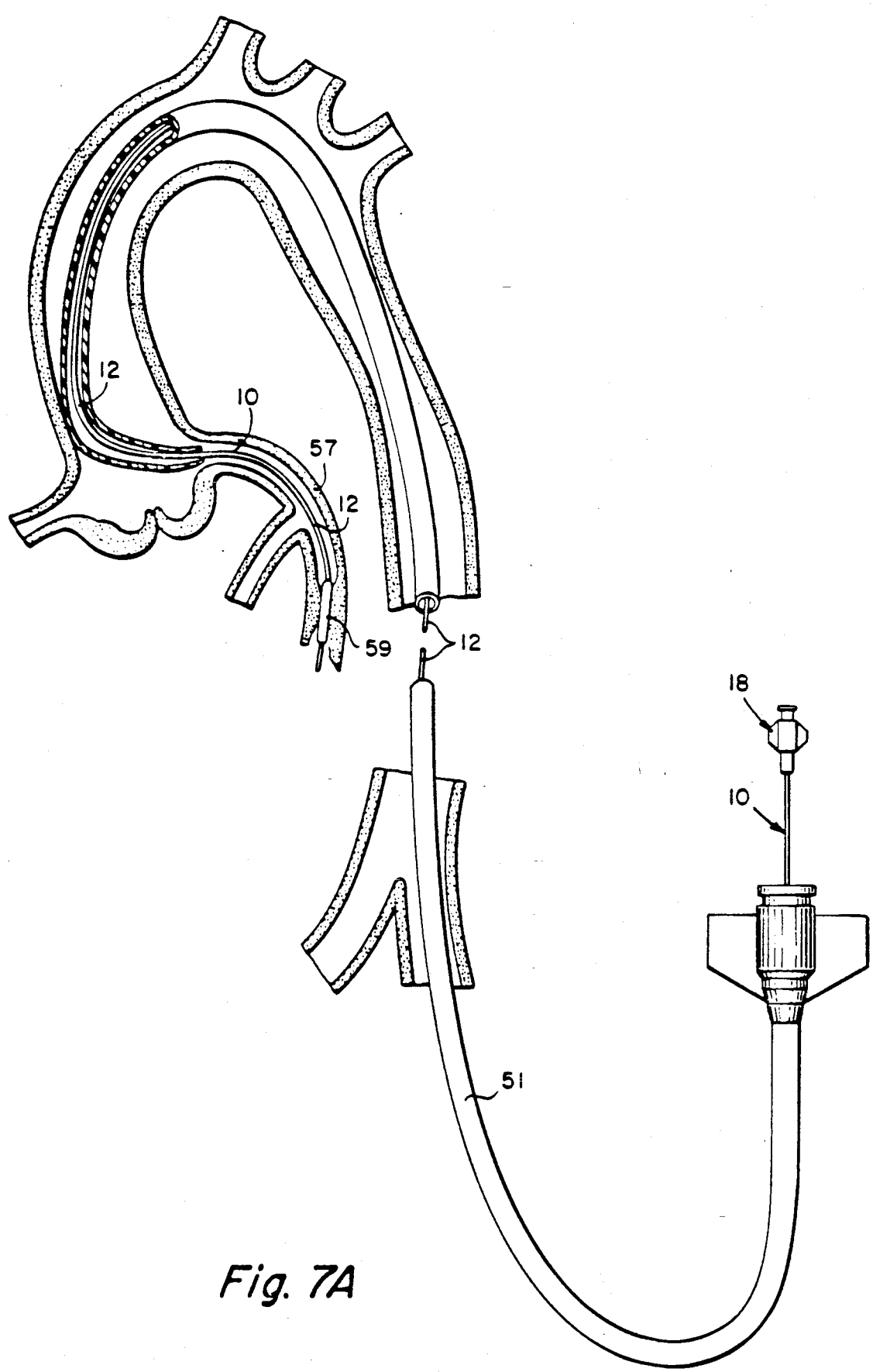
FIG. 7A is a fragmented illustration of a coronary arterial system with a guide catheter in place and a dilatation catheter having a detachable luer fitting extending through the guide catheter and into the stenosis of a coronary artery.
Figure 7B:
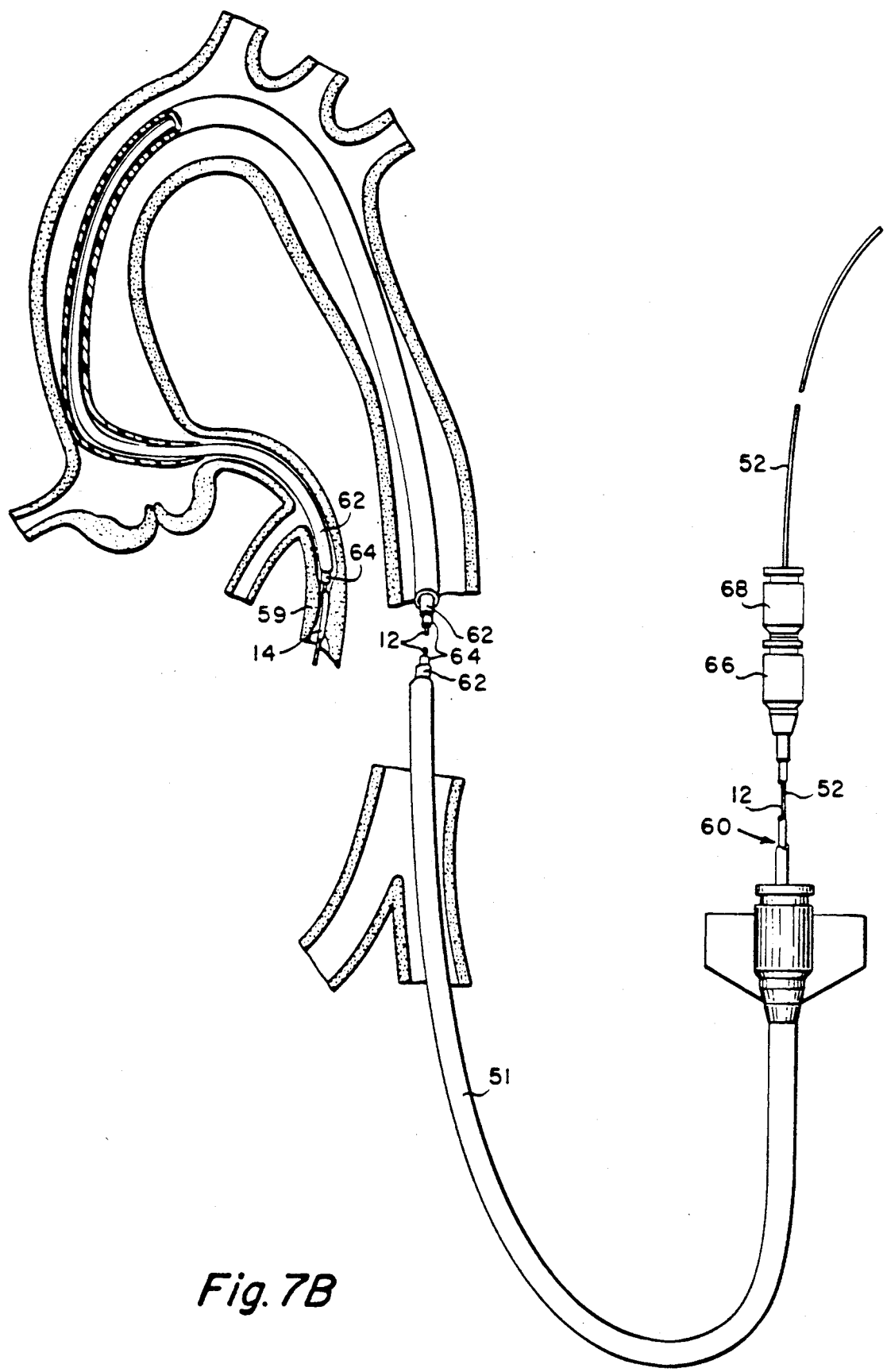
FIG. 7B is an illustration similar to FIG. 7A with the proximal luer fitting of the catheter detached, a guidewire extension attached to the proximal end of the dilatation catheter and the dual guiding sheath arrangement advanced over the balloon dilatation catheter and into the coronary artery in proximity to the stenosis.
Figure 7C:
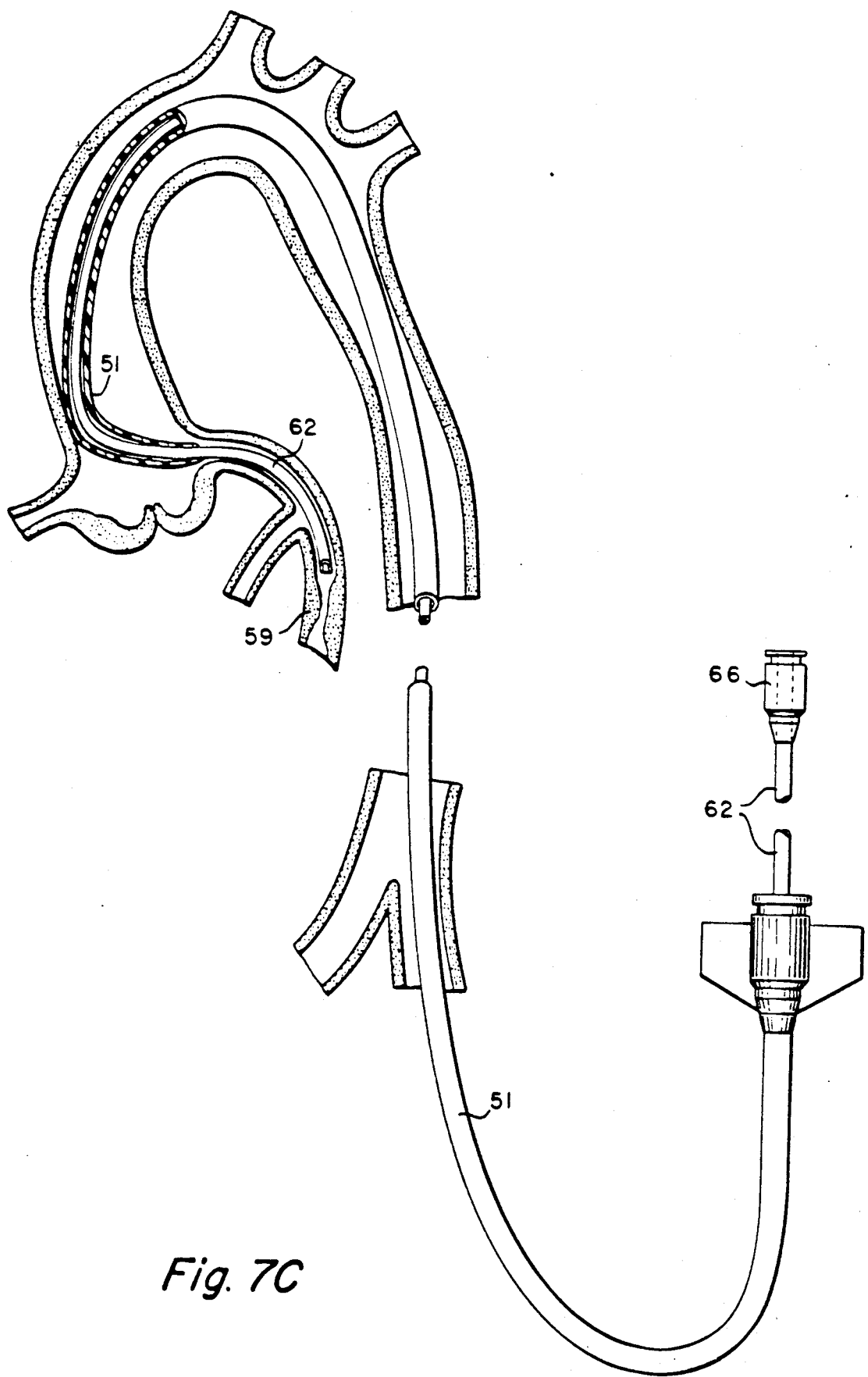
FIG. 7C is an illustration of the arterial and catheter system of FIG. 7B with the dilatation catheter and inner sheath removed, leaving the outer sheath in place and in readiness to receive another dilatation catheter having an integral guidewire.

In another mode of operation, it may be desired to replace the small diameter dilatation catheter 10 with another, small diameter dilatation catheter having an integral guidewire. FIG. 7A illustrates a guide catheter in place in the patient's coronary arterial system and a small diameter dilatation catheter 10 extending through the guide catheter 51, into a coronary artery 57 and into the stenosis 59. Such a catheter exchange requires removal of the initial catheter 10. However, in order to maintain an ability to quickly and easily reach the stenosis with the next catheter, the luer fitting 18 is detached and an extension wire 52 is fitted to the socket 50 at the proximal end of the shaft 12 (FIG. 7B). As shown in FIG. 7B, a tubular guide sheath assembly 60 then is advanced over the extension wire 52 and catheter shaft 12. The sheath assembly 60 is advanced to place its distal end within the coronary artery 57 as close to the stenosis 59 as possible. Once the sheath 60 has been so placed, the catheter 10 may be withdrawn, possibly together with a portion of the sheath assembly as described below. As shown in FIG. 7C, the remaining portion of the guide sheath assembly 60 then provides a clear and direct path along which the replacement catheter may be advanced and guided directly to the stenosis 59.

The foregoing sheath assembly 60 is selected and dimensioned with reference to the catheters that are to be passed through it so that the catheters may pass freely. As discussed below, the guide sheath assembly 60 may be formed in two elements including an inner sheath and an outer sheath. The outer sheath may be used alone with relatively larger diameter catheters and the outer sheath and inner sheath may be used together with very small diameter catheters or guidewires. The inner diameter defined by the sheath arrangement, whether the outer sheath alone or the combination of outer and inner sheath should be such as to permit free passage of the catheter or guidewire with which it is to be used but without having so much clearance that the ability of the sheath to be pushed over such a catheter or guidewire would be impaired.

The guide sheath assembly 60 is illustrated in FIG. 6 and includes an outer sheath 62 and an inner sheath 64 that is received in the outer sheath 62. Each of the outer and inner sheaths 62, 64 is provided with a proximal fitting 66, 68. The fittings ar detachably connectable to each other with luer tapers. The inner sheath 64 serves to fill sufficiently the annular space between the small diameter catheter shaft or guidewire and the inner lumen of the outer sheath 62 to provide axial strength or "pushability" for the sheath assembly as it is advanced over the catheter or guidewire. Of course, if the catheter is of sufficient diameter, the inner sheath 64 may be omitted and the procedure may be effected with the outer sheath alone. When both inner and outer sheaths are used, after the sheath assembly has been advanced into position, the inner sheath 64 is removed to present the full diameter lumen of the outer sheath and to enable insertion of the replacement dilatation catheter 10 with integral guidewire.

As mentioned above in another protocol, the small diameter catheter with integral guidewire may be exchanged for a conventional balloon dilatation catheter having a removable guidewire. The small diameter catheter with integral guidewire may be removed as described above in connection with FIGS. 7A–7C. From the configuration shown in FIG. 7C in which the outer sheath 62 provides a direct path to the stenosis 59, a conventional guidewire is advanced through the sheath 62 so that its distal tip can extend through the stenosis 59. A guidewire extension then is attached to the proximal end of the guidewire. The sheath 62 then may be withdrawn, the guidewire arrangement maintaining position in the stenosis. After the sheath 62 is withdrawn, a conventional over the wire catheter can be passed over the guidewire to direct its distal end directly to the stenosis.

In still another protocol, a conventional dilatation catheter having a removable guidewire may be exchanged for a small diameter catheter having an integral guidewire. In order to exchange that catheter for a catheter having an integral guidewire, a guidewire extension 52 may be attached to the proximal end of the guidewire. The conventional balloon dilatation catheter then may be removed over the extended guidewire. A sheath assembly 60 including both the outer sheath 62 and inner sheath 64 then is advanced over the guidewire to locate the distal end of the outer sheath 62 adjacent the stenosis 59. The inner sheath 64 and guidewire then may be removed leaving the configuration shown in FIG. 7C of an open outer sheath 62 through which the small diameter catheter with integral guidewire may be advanced directly to the stenosis 59.

By way of example, for use with a small diameter dilatation catheter having an integral guidewire shaft where the shaft is of the order of 0.022" diameter and a conventional guidewire having a diameter of the order of 0.016", the outer sheath may be about 125 cm long and be approximately 0.058" outer diameter having a wall thickness of the order of 0.009". The outer sheath 62 is formed to include a proximal portion 67 and a distal portion 69. The proximal portion 67 preferably is formed from high density polyethylene and is stiffer than the distal portion 69 which preferably is formed from a more flexible linear low density polyethylene. The more flexible distal portion is desired so that the outer sheath 62 is flexible and can follow the tortuous coronary anatomy. The proximal section 67 is about 100 cm long and the distal portion 69 is about 25 cm long. The proximal and distal portions 67, 69 are joined at a heat bond, indicated at 70.

A stainless steel helical coil 72 is mounted on the outside of the distal end of the outer sheath 62 and is about 15 cm in length. The spring may be formed from wire about 0.002" diameter and serves to enhance the radiopacity of the distal portion of the outer sheath so that it may be visualized fluoroscopically. The coil 72 preferably is coated with a lubricious material such as a polyurethane silicone blend. The coil 72 is attached only at its ends to the distal section 69 by an appropriate adhesive, preferably cyanoacrylate. The individual coils between the ends of the coil 72 are spaced very slightly from each other so that the distal portion of the outer sheath in the region of the coil 72 remains highly flexible. Upon placement of an axial compressive load on the coil 72, the individual coils butt against each other to form a relatively rigid, inflexible tubular column. This is desirable when withdrawing a balloon catheter through the outer sheath to insure that the balloon, which will interfere with the distal tip of the catheter, will not cause column buckling of the distal tip of the catheter. Should there be sufficient interference between the balloon and the distal end of the catheter to cause any appreciable column compression, the coil 72 rigidifies to provide support. The spacing of the coils should be just sufficient to permit the coil to retain its flexibility when it is not under an axial compressive load. For example, a few ten thousandths of an inch spacing between coils should be sufficient.

A soft distal tip 74 is attached to the distal tip of the distal section 69, distally of the coil 72. The distal tip 74 may project distally of the polyethylene distal section 69 approximately 2.5 mm. It may be formed from a soft elastomeric material, preferably one which is a styrene ethylene/butylene styrene(s-eb-s) block copolymer.

The inner sheath 64 which, for example, may be passed over a 0.016" or 0.018" diameter guidewire is approximately 0.034" outer diameter and may have an inner diameter of the order of 0.026". The distal tip of the inner sheath 64 is tapered. The inner sheath is slightly longer than the outer sheath so that when the inner sheath is advanced fully into the outer sheath, the distal tip of the inner sheath will extend about 1.5 cm beyond the distal tip of the outer sheath.

The luer fittings 68, 66, respectively, of the inner and outer sheaths 64, 62 are injection molded onto the proximal ends of the tubular sheaths. The proximal luer fitting 68 of the inner sheath 64 has a purging port 76 which communicates with the lumen of the luer fitting 66 on the outer sheath when the two sheaths are connected. The purging port 76 permits air to be purged from the inner and outer sheaths simultaneously by flushing saline solution through the proximal luer fitting 68.

From the foregoing, it will be appreciated that the invention provides a means by which catheter and guidewire exchanges can be performed quickly and expediently with minimal risk to the patient and without losing catheter or guidewire position. The invention enables such an exchange to be made for a catheter of the type having an integral, non-detachable guidewire as well as for a conventional movable guidewire catheter. Although the foregoing description of the invention has made reference to balloon dilatation catheters, it should be understood that the advantages of the invention also may be used with other catheters having both movable guidewires and integral guidewires. For example, the invention may be practised to effect catheter changes with laser catheters, heater probe catheters and the like.

It also should be understood, however, that the foregoing description of the invention is intended merely to be illustrative thereof and that other modifications and embodiments may be apparent to those skilled in the art without departing from its spirit.

Having thus described the invention what we desire to claim and secure by letters patent is:

1. A balloon dilatation catheter comprising:
   a tubular shaft having tubular distal and proximal ends and defining a lumen extending therethrough;
   the tubular shaft being torsionally rigid to transmit manipulation of the shaft from its proximal end to movement of its distal end as well as being circumferentially rigid;
   a dilatation balloon mounted to the distal end of the shaft and in communication with the lumen;
   a fitting for communicating with the lumen, the fitting being detachably and securely locked to the proximal end of the shaft, such that manipulation of the fitting by its proximal end moves the distal end of the shaft.

2. A balloon dilatation catheter as defined in claim 1 wherein the fitting comprises a luer fitting.

3. A balloon dilatation catheter as defined in claim 2 wherein said fitting comprises:
   a hollow hub having a passageway extending therethrough and adapted to receive the tubular proximal end of the shaft, the interior of the hub having a distally tapering surface;
   a collet having a central bore therethrough adapted to receive the tubular proximal end of the shaft, the collet being receivable within the bore of the hub, the collet having a plurality of axially extending fingers, the distal ends of the fingers being tapered to mate with the tapered surface in the hub whereby drawing together of the hub and collet will cause the fingers of the collet to constrict tightly about the tubular shaft;
   a luer body threadably connected to the proximal end of the hub, said luer body having means for urging the collet distally into engagement with the tapered surface of the interior of the hub when the luer body and hub are screwed together.

4. A catheter as defined in claim 3 wherein said means comprises:
   a stop member carried by the luer body, the stop member being constructed to engage the proximal end of the tubular catheter shaft to preclude movement of the shaft proximally of the stop member, the stop member having an aperture formed therethrough to permit fluid communication between the lumen in the shaft and the interior of the luer body; and
   a compressible gasket disposed between the stop member and the collet, the gasket having a hole formed therethrough which receives the tubular shaft of the catheter.

5. A catheter as defined in claim 4 wherein the stop member has at its distal face a proximally tapering bore, the proximal end of the taper defining a smaller diameter than the diameter at the proximal end of the tubular shaft.

6. A balloon dilatation catheter as claimed in claim 3, further comprising a compressible gasket having a central bore for receiving the tubular shaft and wherein the luer body has a hollow bore at its distal end adapted to receive the gasket, such that when the luer body and the hub are screwed together, the gasket is compressed and securely grips the tubular shaft.

7. A balloon dilatation catheter as claimed in claim 6, further comprising a stop member with a central bore for receiving the proximal end of the tubular shaft, the stop member being adapted for mounting within the hollow bore of the luer body proximally of the resilient sealing gasket, the stop member limiting proximal movement of the tubular member with respect to the fitting.

* * * * *